United States Patent [19]

Stahly

[11] 4,456,347
[45] Jun. 26, 1984

[54] METHOD AND APPARATUS FOR FACILITATING RELAXATION

[75] Inventor: Frederick A. Stahly, Rochester, N.Y.

[73] Assignee: Limbic Training Systems, Inc., Boulder, Colo.

[21] Appl. No.: 293,619

[22] Filed: Aug. 17, 1981

[51] Int. Cl.$^3$ .............................................. G02C 1/00
[52] U.S. Cl. ...................................... 351/158; 351/41
[58] Field of Search ................... 351/158, 210, 41; 434/236

[56] References Cited

U.S. PATENT DOCUMENTS 2,726,380 12/1955 Campisi .............................. 351/158
3,379,885 4/1968 Nork .................................... 351/158

OTHER PUBLICATIONS

"Survey of Eye Movement Recording Methods", by Laurence R. Young and David Sheena, Behavior Research Methods & Instrumentation, 1975, vol. 7(5), pp. 397-429.

Primary Examiner—John K. Corbin
Assistant Examiner—Rodney B. Bovernick
Attorney, Agent, or Firm—Morton A. Polster

[57] ABSTRACT

A method and apparatus for assisting individuals to achieve the mental and physical relaxation which often characterizes successful meditation. Minute saccadic eye movements are monitored, and the individual is made conscious of any such movement by a sensible signal, such as an audible tone. By reducing undesired saccadic movements, the individual attains the desired state of psycho-physical relaxation. The preferred apparatus, carried by eyeglasses-type support, utilizes reflections of non-visible radiant energy to monitor eye movement.

10 Claims, 5 Drawing Figures

METHOD AND APPARATUS FOR FACILITATING RELAXATION

This invention relates to the control of human psycho-physical activities, and, more particularly, to a method and apparatus for assisting individuals to achieve psycho-physical relaxation, a healthful human state which is sometimes achieved by such complex methods as meditation and yoga.

BACKGROUND OF THE INVENTION

For centuries, many cultures have considered the psycho-physical relaxation which accompanies meditative practices to be an important adjunct to human well being. However, it is only relatively recently that such relaxation has become the subject of serious study in western countries. As the result of such recent studies, western science has begun to confirm age-old beliefs regarding the value and importance of psycho-physical relaxation. Perhaps the most important of the recent scientific findings have been tests which substantiate that the apparent mental and physical relaxation that accompanies meditation is effective in reducing certain undesirable symptoms of emotional stress and physical hypertension.

However, even though meditation has long been understood to have such beneficial effects on human health, it is also well known that the relaxed states which accompany meditation are difficult to achieve. Long and arduous training programs under gurus, Zen masters, Transcendental Meditation leaders, etc., are commonly considered necessary, and even with such help many people are not successful.

The subject invention greatly facilitates attainment of psycho-physical relaxation, and although it achieves this important result in a remarkably simple manner, it can only be fully appreciated and understood in the context of the basic human psycho-physiology to which it intimately relates. Of course, no attempt will be made to provide a detailed description of the complex anatomical system involved. Instead, the following background will comprise a relatively short and somewhat over-simplified summary of a human behavioral model which the inventor has recently developed. This model is supported by his analysis of an extensive number of scientifically accepted human and animal studies conducted over the past century and, insofar as concerns prior art, the most pertinent of these studies were those of Trigant Burrow.

All animal life appears to be directed by a brain and nerve activity which the inventor prefers to identify by the term "central processor." The central processor is the source of instructions for the body's efferent neural activity which controls the muscle actions and other body cell responses that in turn determine the body's movements, heart beat, blood pressure, temperature, etc. Such efferent activity often is directed by the central processor in response to afferent neural activity, the latter being generated in response to outside stimuli sensed by the individual's eyes, ears, nose, skin, muscles, etc. Response to such external stimuli is essential to the survival of the individual.

However, an individual's response to outside stimuli is very selective, and it varies according to priorities programmed by the central processor. In most animals, highest priority appears to be given to stimuli representing immediate threats to survival, generally those activating the "fight-flight" response (except that, in the defenseless very young, the sounds or smells of a parent may dominate all other external stimuli, keeping the infant close to the parent and its protection). These higher priority responses take precedence over normal, body-regulating neural activities (those which operate to satisfy the body's needs for rest, nourishment, sex, etc.).

While this priority system seems to function adequately in lower animals, in humans it appears to have malfunctioned, resulting in the development of unconscious abberant behavior—a pandemic disease—of which we are unaware but which causes unnecessary neurosis, stress and hypertension. This malfunction of priorities has apparently arisen from the human use of symbols and language: Human infants are initially conditioned to give priority to efferent neural activity initiated by semiotic (verbal, language-oriented) inputs from their parents and, after infancy, such semiotically-induced efferent activity continues to dominate and take precedence over many basic efferent activities (heart beat, blood pressure, etc.) which, in the absence of such language-oriented stimuli, would instead be normally controlled in a more healthful manner by the central processor.

An example of the unhealthy effects of such improper prioritization can be seen in the changes which often occur in efferent neural activity in response to internal stimuli such as imagined or remembered "mental" images. For instance, a remembered insult can cause the individual's heart beat to increase, and blood pressure to rise. Further, the individual is often not consciously aware of such internal stimuli. For instance, certain external stimuli, such as the tone of another's voice or an expression on another's face which, while intended by that other person to be neutral or pleasant, may unconsciously remind an individual of a past insult from a third person, thereby triggering efferent neural activity in the individual which generates psycho-physical responses characteristic of hostility. Such an unconsciously hostile response to a neutral stimuli is merely one extremely simple example of a type of undesireable efferent activity which, if given proper priority by the central processor, could be eliminated to improve the individual's relations to others, as well as enhancing the well being of the individual by lowering blood pressure, reducing symptoms of stress, etc.

Of particular pertinence to the invention herein is that portion of the inventor's theory which incorporates eye movements into the human behavioral model roughly summarized above.

A great deal of research has been done in the past decade relating to the extremely fast movements of the human eye (saccadic movements) in well-defined patterns responding to brain signals of which the individual may or may not be aware. This research has been significantly enhanced by the development of sophisticated and complex electronic apparatus which can monitor and plot the exact patterns of eye movements, many of which are micro-saccadic (of milliseconds in duration over distances measured in microns). With the help of this complex apparatus, eye movement research has developed devices for exactly monitoring eye position for many different practical purposes, e.g., eye movements are now used for such remote control purposes as aiming the guns of fighter airplanes, and for permitting quadraplegics to activate electronic control switches (to turn on and off lights, TV sets, etc.), and even to operate electronic typewriters. Further, complex devices for monitoring eye position are used in bio-feedback arrangements to help re-train wayward eyes in persons suffering from amblyopia.

One interesting fact which continues to appear in recent eye motion research studies is the prevalence of saccadic eye movements of which the individual is not aware. The relation of such unconscious eye movement to other psycho-physical activities is not well understood, but, based upon the studies of Trigant Burrow (done more than fifty years ago) and based upon the inventor's own studies and his analysis of much recent research in this area, the inventor believes that such micro-saccadic movements are intimately related to the type of mixed-up priorities described above which initiate superfluous neural activities inimical to the individual's well being. Namely, the inventor believes that by learning to control such micro-saccadic eye movement, an individual can still the superfluous neural activity which interferes with the other psycho-physical responses necessary to the individual's well being. In this manner, the individual may be able to achieve clearer and more efficient physical and mental behavior.

The value of stilling superfluous neural activity has been long recognized in such well known practices as the arts of Zen swordsmanship, archery, calligraphy, etc., but, as noted above, such control is known to be difficult to achieve and only after long and arduous study under "masters."

In the course of his own studies relating to eye movement, the inventor has discovered that individuals can be trained to reduce their micro-saccadic eye movements and that such reduced eye movement is accompanied by indications of psycho-physical relaxation which are normally achieved only by persons trained in the art of meditation.

The invention herein is a simple method, carried out with relatively inexpensive apparatus, which can be used by individuals to train themselves to minimize the involuntary micro-saccadic movements of their eyes and, thereby, to readily achieve the kind of therapeutic psycho-physical relaxation that is normally associated with meditation.

SUMMARY OF THE INVENTION

The method and apparatus disclosed herein monitor an individual's eye movements, providing a sensible signal (e.g., visual, audio, or tactile) whenever the amplitude of eye movement exceeds some predetermined amount which can be changed for training purposes. (The term "amplitude" as used herein is intended to refer to any measurable duration of micro-saccadic eye movement.) For instance, when one first begins to use the inventive method for learning to relax, only longer eye movements should be used to generate a signal. However, as training progresses and the individual learns to minimize these initially-monitored movements, the predetermined amplitude can be gradually altered to monitor shorter eye movements, further enhancing the relaxation achieved.

In the preferred embodiments, the monitoring is accomplished, relatively unobtrusively, by means of "light" (radiant energy outside the visible spectrum) directed at the closed or open eye of the individual. The light is delivered from a light-emitting diode (LED) mounted on the frame of an eye-glass-type support. Radiant energy reflected from the surface of the individual's eye or eyelid is received by a photocell. By well known electronic circuitry, any relatively rapid change in the radiant energy reflected to the photocell produces a change in its electrical output signal and, if this change in signal exceeds some preset amplitude, the system generates an audio sound or tactile vibration which can be sensed by the individual. It should be noted that the apparatus of the invention is much simpler than the prior art devices referred to above. It does not monitor eye position but rather is sensitive only to movement of any kind in any direction. Further, as distinguished from other methods using radiant energy to monitor eye movements, the light may be directed at either the closed or open eye, and there is no need to make the difficult apparatus adjustments required by prior art devices which often must sense reflections from the limbus, i.e., being carefully adjusted to monitor the line between the iris and the scelera of the eye.

Much of the simple electronic circuitry referred to above, including the transducers providing the sensible signal for indicating eye movement, is preferably incorporated into the frame and/or temple sections of a pair of special eye glasses. It has been found that, in spite if its size and position, the apparatus is relatively unobtrusive and can be used to carry out the inventive relaxation method either with closed or open eyes and even while sitting quietly watching and listening to a television program or engaging in conversation. The individual is instructed to reduce eye movement, and the absence of signal indicates when that is achieved. As eye movement is reduced, relaxation is greatly enhanced. (Note: While this preferred embodiment utilizes radiant energy to detect saccadic movement, the method disclosed herein also contemplates other means, e.g., physical contact apparatus to detect such undesirable eye motion.)

The value of such relaxation is well known, particularly for the large number of persons who suffer from hypertension, stress, etc. However, the inventor wishes to emphasize that he believes the invention has much wider and, in his opinion, much more important potential: Namely, the invention can be used to train an individual to gain control over superfluous neural activity in the individual's central nervous system.

The invention herein can help individuals achieve such control in a relatively simple and inexpensive manner.

DETAILED DESCRIPTION

The following detailed description of the invention will make reference to the accompanying drawings in which FIG. 1 is a perspective view of one-half of a pair of eyeglass-type support showing the primary elements of apparatus in accordance with the invention;

Figure 1:
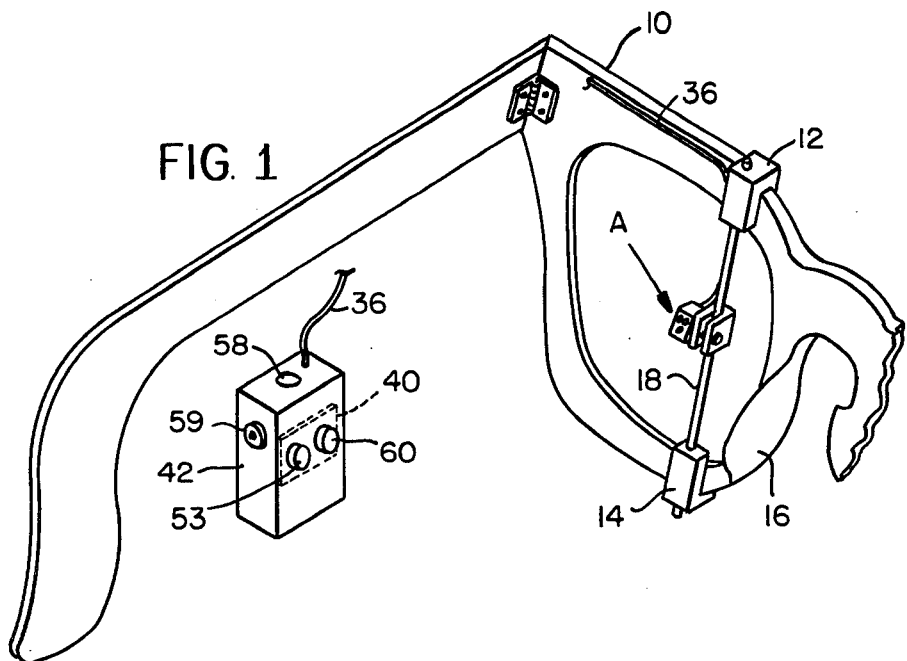

Referring first to FIG. 1, the frame 10 of a pair of eyeglass supports is fitted with a pair of clip units 12,14 which clamp tightly to frame 10 near nosepiece 16. A support rod 18 is fixed to clip unit 14 and is slidably received through clip unit 12 to accomodate frames of varying sizes. The just-described clamping means also includes a set screw (not shown) to tighten support rod 18 in clip unit 12 following appropriate adjustment to mount the unit on frame 10.

Figure 2:
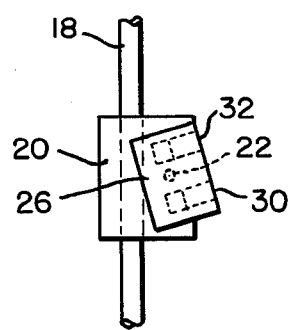
FIG. 2 is a side view of the light-transducing elements designated generally by the letter "A" in FIG. 1.
Figure 3:
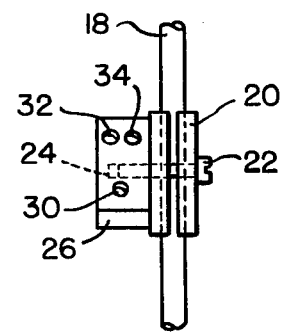
FIG. 3 is a front view (as viewed from the wearer's eye) of the same light-transducing elements shown in FIG. 2.

Light transducing elements, designated generally at "A" in FIG. 1, are attached to support rod 18 by the apparatus illustrated in FIGS. 2 and 3. A split block 20 fits around support rod 18 and is slidable thereon. Adjustment screw 22 passes through split block 20 and is received by a threaded hole 24 in a mounting unit 26.

Three light transducing elements comprising an infrared radiator in the form of a light-emitting diode (LED) 30 and a pair of infrared-sensitive photo diodes 32,34 are supported in mounting unit 26. These light-transducing elements are connected by appropriate wiring 36 to a small electronic circuit 40 held in pocket unit 42 and powered by a small battery (not shown).

To position the light-transducing elements relative to the eye of the wearer, adjustment screw 22 is loosened and split block 20 may be moved along and/or rotated around support rod 18. Also, mounting unit 26 can itself be rotated about the axis of adjustment screw 22 which is tightened to hold the entire mounting apparatus in place following such adjustment.

The elements A are adjusted so that radiant energy from LED 30 is directed to the surface of the eye 44 (FIG. 4) (or the closed eyelid) of the wearer and so that reflections of that radiation are received by photodiodes 32,34.

To improve the life of the battery, it is contemplated that simple and well known gating circuitry (not shown) can be used to energize LED 14 only during a small part of each transmission cycle which can operate at any rate appropriate to the generation of sufficient reflected radiation.

Any slight movement of the individual's eye causes a change in the reflectivity of the particular area of the individual's eye or closed eyelid on which the radiant energy is impinging. For instance, any resulting alteration of the patterns of tiny blood vessels in the sclera, or any minute modifications in the contours of an eyelid, will result in respective changes in such reflectivity.

Any such minute change in reflectivity is accompanied by a corresponding change in the output signals of photodiodes 32,34 which vary in amplitude in accordance with the size and duration of the saccadic movement.

Figure 4:
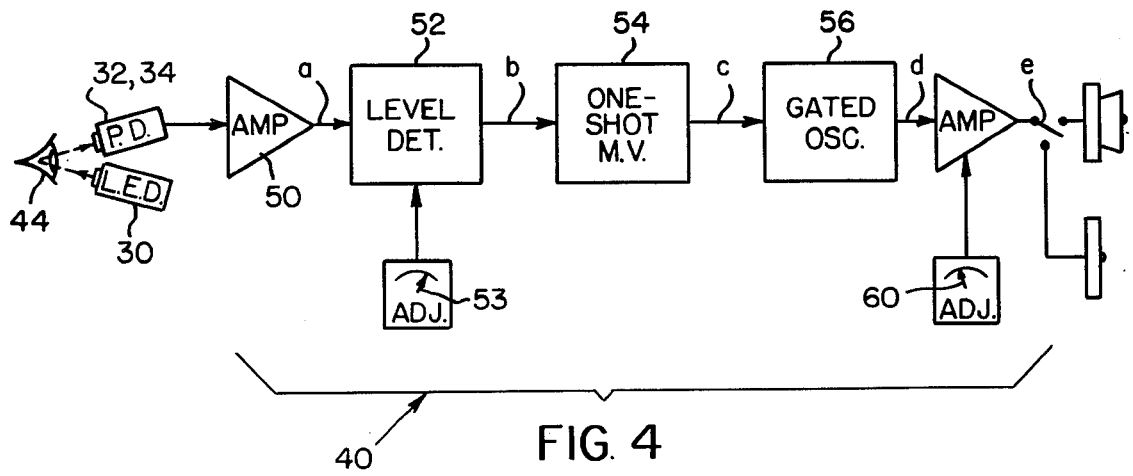
FIG. 4 is a schematic and block diagram showing the basic elements of the apparatus and the interconnecting electronic circuitry.
Figure 5:
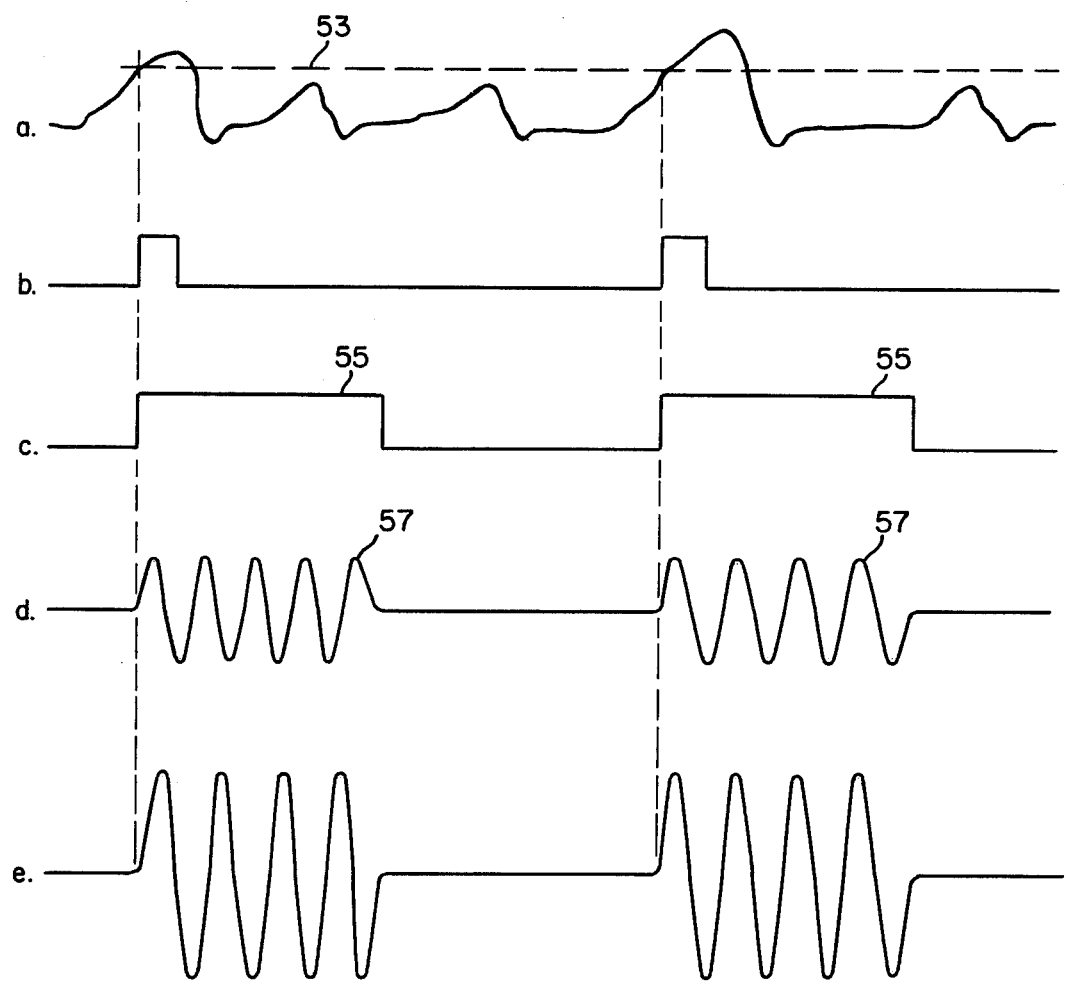
FIG. 5 is a wave-form diagram tracing the generation of electrical signals at the variously lettered outputs indicated in FIG. 4.

Referring now to FIGS. 4 and 5, the output of the photodiodes passes through an amplifier 50 and is fed to a level detector 52 which can be adjusted by knob 53 (FIG. 1) for increasing sensitivity as the wearer's ability to control eye movement improves. Whenever the amplitude of an eye movement exceeds the predetermined level 53 (FIG. 5) set in detector 52, a one-shot multivibrator 54 is energized for a selected period 55 (FIG. 5), and this in turn activates a gated oscillator 56 which generates an appropriate audio signal 57 (FIG. 5) until such time as multivibrator 54 returns to its initial state.

The resulting burst of audio energy activates an appropriate transducer, either a small audio speaker 58 or a tactile "buzzer" 59, which can be heard or felt, respectively, by the wearer. The level of the audio or tactile signal can be appropriately adjusted by a knob 60.

While the inventor believes that the eyeglass-type apparatus just described above is preferred for carrying out the inventive method, it should be understood that other apparatus may also be used. For instance, it is possible to replace the radiant energy transducers with known pressure-sensitive devices which can be appropriately taped to the individual's eyelid. Such apparatus, while more difficult to use, still permits an individual to use the inventive method to monitor and reduce saccadic movements to facilitate attainment of a relaxed mental and physical state comparable to that achieved by successful meditation.

What is claimed is:

1. The method of facilitating psycho-physical relaxation by an individual comprising the steps of:
   (a) monitoring saccadic movements of one of the individual's eyes;
   (b) determining when any such movement exceeds a predetermined amplitude;
   (c) providing a signal, sensible to the individual, whenever movement of the individual's eye exceeds the predetermined amplitude; and
   (d) instructing the individual to modify the sensible signal by reducing eye movement.

2. The method of claim 1 wherein the monitoring step comprises the further steps of:
   (i) directing radiant energy toward the individual's eye; and
   (ii) sensing reflections of said radiant energy.

3. The method of claim 1 wherein the step of providing a sensible signal comprises activating an audible transducer.

4. The method of claim 1 wherein the step of providing a sensible signal comprises activating a tactile transducer.

5. Apparatus for facilitating psycho-physical relaxation by an individual comprising
   monitoring means for providing an output responsive to the saccadic movement of one of the individual's eyes;
   detection means for determining when any such eye movement exceeds a predetermined amplitude; and
   transducer means for producing a signal sensible to the individual and indicative of an eye movement exceeding the predetermined amplitude.

6. The apparatus of claim 5 wherein said monitoring means comprises
   radiator means for directing radiant energy at the individual's eye; and
   radiation-sensitive means responsive to reflections of said radiation.

7. The apparatus of claim 5 further comprising
   support means for positioning the monitoring means in proximity to the individual's eye.

8. The apparatus of claim 7 wherein said support means comprises an eyeglass-type frame member.

9. The apparatus of claim 7 wherein said support means comprises clamp means for attaching support means to the frame of a pair of eyeglasses.

10. The apparatus of claim 9 wherein said support means further comprises a mounting unit for receiving said radiator means and said radiation-sensitive means, said mounting unit being adjustably positioned on said clamp means.

* * * * *